United States Patent
Lynn

(10) Patent No.: US 11,045,571 B1
(45) Date of Patent: Jun. 29, 2021

(54) REDUCED NOISE AIR DECONTAMINATOR

(71) Applicant: Daniel W. Lynn, Omaha, NE (US)

(72) Inventor: Daniel W. Lynn, Omaha, NE (US)

(*) Notice: Subject to any disclaimer, the term of this patent is extended or adjusted under 35 U.S.C. 154(b) by 0 days.

(21) Appl. No.: 17/200,799

(22) Filed: Mar. 13, 2021

(51) Int. Cl.
*A61L 9/12* (2006.01)
*A61L 9/015* (2006.01)

(52) U.S. Cl.
CPC .............. *A61L 9/122* (2013.01); *A61L 9/015* (2013.01); *A61L 2209/134* (2013.01); *A61L 2209/212* (2013.01)

(58) Field of Classification Search
CPC .............. A61L 9/12; A61L 9/122; A61L 9/015
See application file for complete search history.

(56) References Cited

U.S. PATENT DOCUMENTS

| | | | |
|---|---|---|---|
| 1,363,589 A | 12/1920 | Hartman | |
| 6,153,105 A | 11/2000 | Tadlock et al. | |
| 6,334,328 B1 | 1/2002 | Brill | |
| 6,685,825 B1 | 2/2004 | Chang | |
| 8,071,526 B2 | 12/2011 | Lynn | |
| 8,075,705 B2 | 12/2011 | Lynn | |
| 9,068,149 B2 | 6/2015 | Lynn | |
| 9,151,528 B2 | 10/2015 | Erbs et al. | |
| 9,174,845 B2 | 11/2015 | Lynn | |
| 9,522,348 B2 | 12/2016 | Lynn | |
| 10,314,932 B2 * | 6/2019 | Huang | A61L 2/14 |
| 10,426,855 B2 | 10/2019 | Lynn | |
| 2003/0156978 A1 | 8/2003 | Gillette | |
| 2004/0004042 A1 | 1/2004 | Hadley et al. | |
| 2004/0168989 A1 | 9/2004 | Tempest | |
| 2009/0142225 A1 | 6/2009 | Tornqvist | |
| 2010/0219137 A1 | 9/2010 | Lacasse | |
| 2013/0193081 A1 | 8/2013 | Vasiliu et al. | |
| 2013/0341285 A1 | 12/2013 | Marion | |
| 2014/0027388 A1 | 1/2014 | Constant | |
| 2014/0263097 A1 | 9/2014 | Lynn | |
| 2016/0251243 A1 | 9/2016 | Lynn | |

* cited by examiner

*Primary Examiner* — Robert A Hopkins
(74) *Attorney, Agent, or Firm* — Nasr Patent Law LLC; Faisal K. Abou-Nasr

(57) ABSTRACT

A reduced noise air decontaminator includes an enclosure with a removably coupled lid that includes a vent. One or more ozone generators are disposed within the enclosure and configured output gaseous ozone. One or more ozone output tubes are fluidically coupled to the one or more ozone generators. The one or more ozone output tubes are configured to release the gaseous ozone within the enclosure. A fan is also disposed within the enclosure. The fan is configured to blow the gaseous ozone through the vent in the lid. The fan is coupled to a support frame configured to suspend the fan over the one or more ozone output tubes and at a distance from the lid in order to prevent or reduce lid vibrations cause by fan movement when the fan blows the gaseous ozone through the vent in the lid.

20 Claims, 8 Drawing Sheets

REDUCED NOISE AIR DECONTAMINATOR

TECHNICAL FIELD

The present disclosure relates to systems for improving air quality, and more particularly, to an air decontaminator.

BACKGROUND

Odors may arise from the decomposition products of meat or fish protein, containing sulfur, nitrogen, and oxygen, as well as spoilage microorganisms that belong to four major groups: bacteria, viruses, protozoa, or fungi. Odors can also arise from fires, (incomplete combustion), fats, chemicals, etc. The smells that humans react to most strongly are associated with food odor sensations which are often the result of a complex interaction of many, sometimes hundreds, of chemical compounds on the sensory organs of the nose. The smell in a modern office building is a "cocktail" made up of the smells of more than a thousand substances (sweat, tobacco, carpeting, cleansers, plants, ink, etc.).

The total smell perceived is often different from, and sometimes stronger than, the sum of its parts. Bad smells can cause health effects, such as headache, nausea, and sleeplessness. Bad odor compounds are generally not poisonous, at least not in the concentrations at which they begin to cause an odor nuisance. If the concentration of an odor in air is below levels of irritation (levels known to cause eye, nose, or throat irritation in people), the symptoms will pass when you move out of the exposure area. However, if the concentration of an odor in air is at or above levels of irritation and the exposure duration is longer, the symptoms may last after moving out of the exposure area.

Circulated air may also become infected with pathogens (e.g., bacteria, viruses, etc.), resulting in transmission of infectious diseases within an environment. At high enough concentrations, pathogens in circulated air can pose a serious health risk to occupants of an environment (e.g., a hotel, restaurant, grocery store, department store, office building, single/multi-family residential building, hospital, school, arena, concert/event hall, airplane cabin, bus, train, etc.).

To effectively prevent symptoms from unpleasant odors and provide a clean and safe environment, there is a need for systems that can safely deodorize and disinfect air being circulated within environment.

Many types of devices have been previously provided to reduce odors in indoor areas such as restaurant kitchens, bathrooms, grocery stores, classrooms, school locker rooms, office buildings, homes, veterinary clinics, hospitals, hotels, etc. However, most existing devices utilize chemicals or masking deodorizers. Further, the existing deodorizing devices are typically unable to disinfect air and contact surfaces while deodorizing the area in which the existing deodorizing devices are placed. The existing deodorizing devices are also limited in their ability to treat bacteria, viruses, mildew, molds, allergens, smoke odors, or food preparation odors.

Common inorganic agents, such as sodium hypochlorite, hydrogen peroxide, and potassium permanganate can readily oxidize most of the usual odor compounds. In general, the cheapest of these is sodium hypochlorite (chlorine bleach). The extent of poisoning caused by chlorine depends on the amount of chlorine a person is exposed to, how the person was exposed, and the length of time of the exposure. When chlorine gas comes into contact with moist tissues, such as the eyes, throat, and lungs, an acid is produced that can damage these tissues. Industrially, hydrogen peroxide has been used for years to deodorize, disinfect, and neutralize hazardous pollutants.

Ozone is also a very powerful oxidizing agent and is safe for humans when the time and amount of exposure is controlled. Ozone in water decomposes to oxygen and hydroxyl radicals, each of which has a higher oxidation potential than either ozone or chlorine. The activity of hydroxyl radical is enhanced by a higher pH. Ozone can oxidize odorous organic and inorganic compounds in the presence of water. Also, in the presence of moisture, it is a powerful germicide. Ozone can also directly oxidize odorous compounds by attacking double bonds or a reactive site. Thus, ozone may be used to reduce odors and disinfect air/surfaces without the current limitations of existing deodorizing and/or disinfecting devices.

SUMMARY

Aspects of this disclosure are directed to a reduced noise air decontaminator. In embodiments, the air decontaminator includes an enclosure with a removably coupled lid that includes a vent. One or more ozone generators are disposed within the enclosure and configured output gaseous ozone. One or more ozone output tubes are fluidically coupled to the one or more ozone generators. The one or more ozone output tubes are configured to release the gaseous ozone within the enclosure. A fan is also disposed within the enclosure. The fan is configured to blow the gaseous ozone through the vent in the lid. The fan is coupled to a support frame configured to suspend the fan over the one or more ozone output tubes and at a distance from the lid in order to prevent or reduce lid vibrations cause by fan movement when the fan blows the gaseous ozone through the vent in the lid.

This Summary is provided solely as an introduction to subject matter that is fully described in the Detailed Description and Drawings. The Summary should not be considered to describe essential features nor be used to determine the scope of the Claims. Moreover, it is to be understood that both the foregoing Summary and the following Detailed Description are example and explanatory only and are not necessarily restrictive of the subject matter claimed.

BRIEF DESCRIPTION OF THE DRAWINGS

The detailed description is described with reference to the accompanying figures. The use of the same reference numbers in different instances in the description and the figures may indicate similar or identical items. Various embodiments or examples ("examples") of the present disclosure are disclosed in the following detailed description and the accompanying drawings. The drawings are not necessarily to scale. In general, operations of disclosed processes may be performed in an arbitrary order, unless otherwise provided in the claims.

DETAILED DESCRIPTION

Reference will now be made in detail to the subject matter disclosed, which is illustrated in the accompanying drawings.

Embodiments of this disclosure are directed to a system for disinfecting air with ozone ($O_3$) gas. Ozone is a powerful oxidizing agent that is safe for humans as long as the amount of ozone per unit volume of air is kept within a certain range (e.g., 0.01 to 0.3 ppm, or more particularly 0.05 to 0.2 ppm). At higher concentrations, it may be necessary to control a length of time that humans/animals are exposed and/or type of activity taking place in the ozone-enriched environment. For example, OSHA guidelines for ozone in the workplace are as follows: 0.2 ppm for no more than 2 hours exposure; 0.1 ppm for 8 hours per day exposure doing light work; 0.08 ppm for 8 hours per day exposure doing moderate work; and 0.05 ppm for 8 hours per day exposure doing heavy work.

Ozone in water decomposes to oxygen and hydroxyl radicals, each of which has a higher oxidation potential than either ozone or chlorine. The activity of hydroxyl radical is enhanced by a higher pH. Ozone can oxidize odorous organic and inorganic compounds in the presence of water. Also, in the presence of moisture, it is a powerful germicide. Ozone can also directly oxidize odorous compounds by attacking double bonds or a reactive site. Thus, ozone may be used to reduce odors and disinfect air/surfaces without the current limitations of existing deodorizing and/or disinfecting devices. The amount of ozone required may depend on the odor levels being controlled and operational safety parameters (e.g., occupancy, exposure time, types of activity, etc.) of an environment (e.g., a hotel, restaurant, grocery store, department store, office building, single/multi-family residential building, hospital, school, arena, concert/event hall, airplane cabin, bus, train, etc.).

FIGS. 1 through 8 illustrate an air decontaminator 100 configured to disinfect and/or deodorize ambient air by releasing gaseous ozone into the air. The air decontaminator 100 is structurally configured in a manner that has certain advantages over existing systems. Namely, the air decontaminator 100 includes mechanisms to prevent or reduce noise from lid vibrations caused by fan movement when the air decontaminator is blowing ozone into the air.

Figure 1:
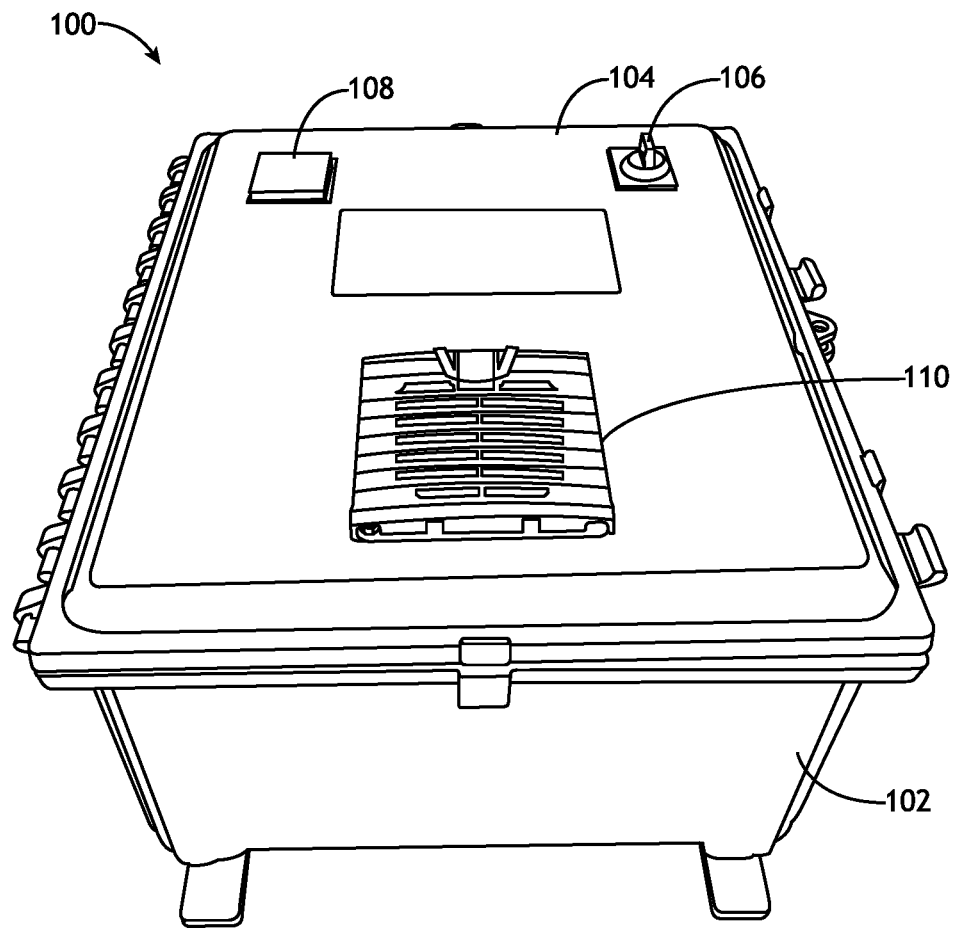
FIG. 1 is a perspective front view of an air decontaminator, in accordance with one or more embodiments of this disclosure.
Figure 2:
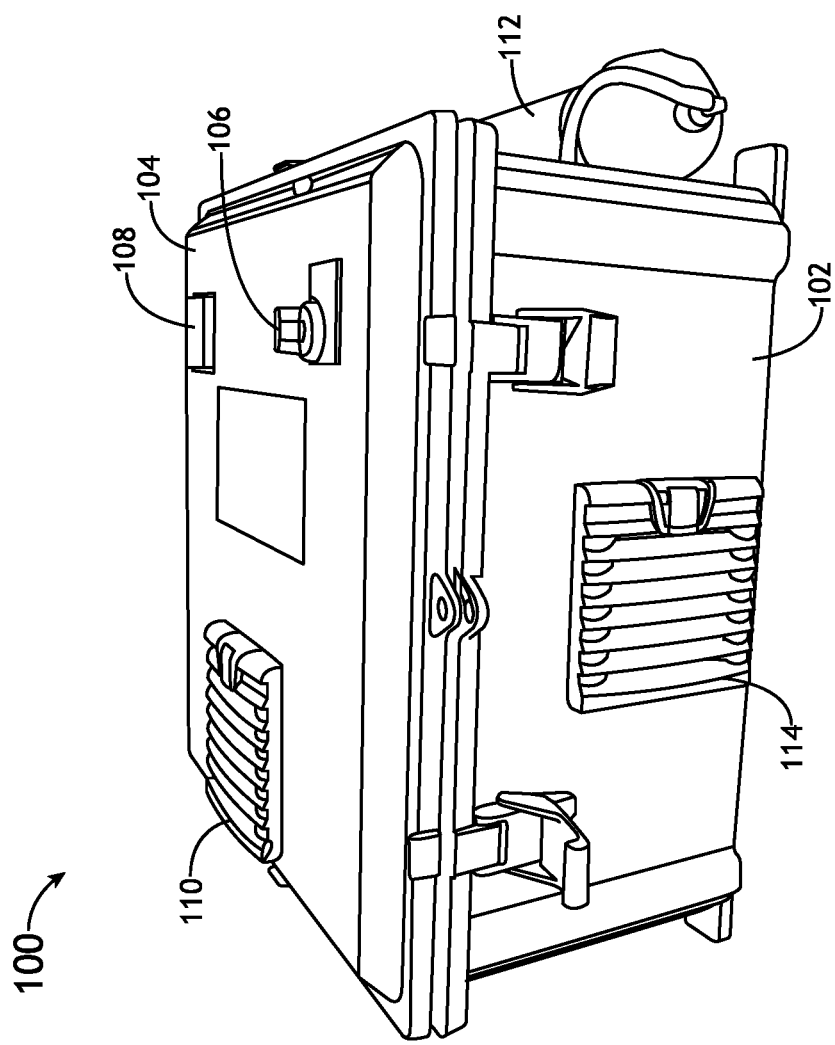
FIG. 2 is a perspective right side view of the air decontaminator of FIG. 1, in accordance with one or more embodiments of this disclosure.

As shown in FIGS. 1 and 2, the air decontaminator 100 includes an enclosure 102 with a removably coupled lid 104. The lid 104 is configured to enclose (e.g., when secured/closed) and provide access to (e.g., when removed/opened) the components housed in an interior portion of the enclosure 102. In some embodiments, the lid 104 may be secured to the enclosure 102 by at least one hinge on a first side and at least one latch or fastener on a second (e.g., opposing) side. However, in other embodiments, the lid 104 may be secured to the enclosure 102 by any number or type of fasteners (e.g., screws to mate with bores in the enclosure 102, hinges, latches, interference fittings, slide rails, threaded fasteners, clipping fasteners, magnetic fasteners, or the like). The lid 104 may be "removably coupled" to the enclosure 102 in the sense that the lid 104 is hingedly coupled to the enclosure 102, slidably coupled to the enclosure 102, rotatably coupled to the enclosure 102, or completely removable from the enclosure 102 in order to access internal components of the air decontaminator 100.

In embodiments, the lid 104 includes an electrical switch 106 configured to power on/off the air decontaminator 100. For example, the electrical switch 106 may be toggled between open and closed positions to turn on/off the air decontaminator. It is noted that in some circuit configurations, the open and closed switch settings may be reversed so that the open position corresponds to "ON" and the closed position corresponds to "OFF". Thus, to avoid confusion, the settings are hereinafter referred to as ON or OFF positions.

In some embodiments, the electrical switch 106 is a timer switch that can be set to power on the air decontaminator 100 for a predetermined, user-input, and/or programmed amount of time. For example, the electrical switch 106 may include a mechanical timer circuit that holds the electrical switch 106 in the ON position for a selected amount of time (e.g., 15 minutes, 30 minutes, 45 minutes, 1 hour, 2 hours, etc.) before toggling the switch back to the OFF position. Alternatively, the electrical switch 106 may include a digital timer circuit that is programmable through a user interface device 108 (e.g., a display with buttons, dials, and/or switches, a touchscreen display, or any other human machine interface (HMI) device). In embodiments, the user interface device 108 may be configured to receive a runtime input (e.g., a user-selected or user-input runtime) through the HMI. The user interface device 108 may include a controller (e.g., microcontroller, microprocessor, or any other programmable logic device (PLD)) that is configured to electronically toggle the electrical switch to the ON position for the runtime before electronically toggling the electrical switch back to the OFF position. In some embodiments, the electronic toggling may be accomplished by outputting a control/power signal corresponding to the ON position and ceasing to output the control/power signal to indicate the OFF position.

In further embodiments, the electrical switch 106 may be configured to toggle between ON, OFF, and TIMER positions. In such embodiments, the ON or OFF positions can be used to manually power on/off the air decontaminator 100, and the TIMER position (or positions) can be used to power on the air decontaminator 100 for user-selected or user-input runtime either through the user of a digital or mechanical timer circuit. In the case of a mechanical timer, the electrical switch 106 may be turned to select a TIMER position that corresponds to a selected runtime. In the case of a digital timer, the electrical switch 106 may be turned or toggled to a TIMER position that connects with the user interface device 108 so that the user interface device 108 can be used to select or input a runtime for the air decontaminator 100.

The lid 104 includes a vent 110 through which gaseous ozone may be released from the air decontaminator 100. In some air decontaminators, the lid 104 includes a fan that is coupled to the lid 104 (directly behind the vent 110); however, this arrangement of components often results in noisy operation because the fan movement causes the lid 104 to vibrate against the enclosure 102. To reduce noise by preventing or reducing lid vibrations, the presently disclosed air decontaminator 100 does not have a fan coupled to the lid 104. Instead, as shown in FIGS. 4 through 8, the air decontaminator 100 includes a fan 130 that is suspended below the vent 110 by a support frame 132 that is coupled to an inner surface of the enclosure 102. As shown in FIG. 2, the enclosure 102 may also include a side vent 114 (e.g., an exhaust vent) to bring cool air into the enclosure 102 and/or remove hot air from the enclosure 102.

Figure 3:
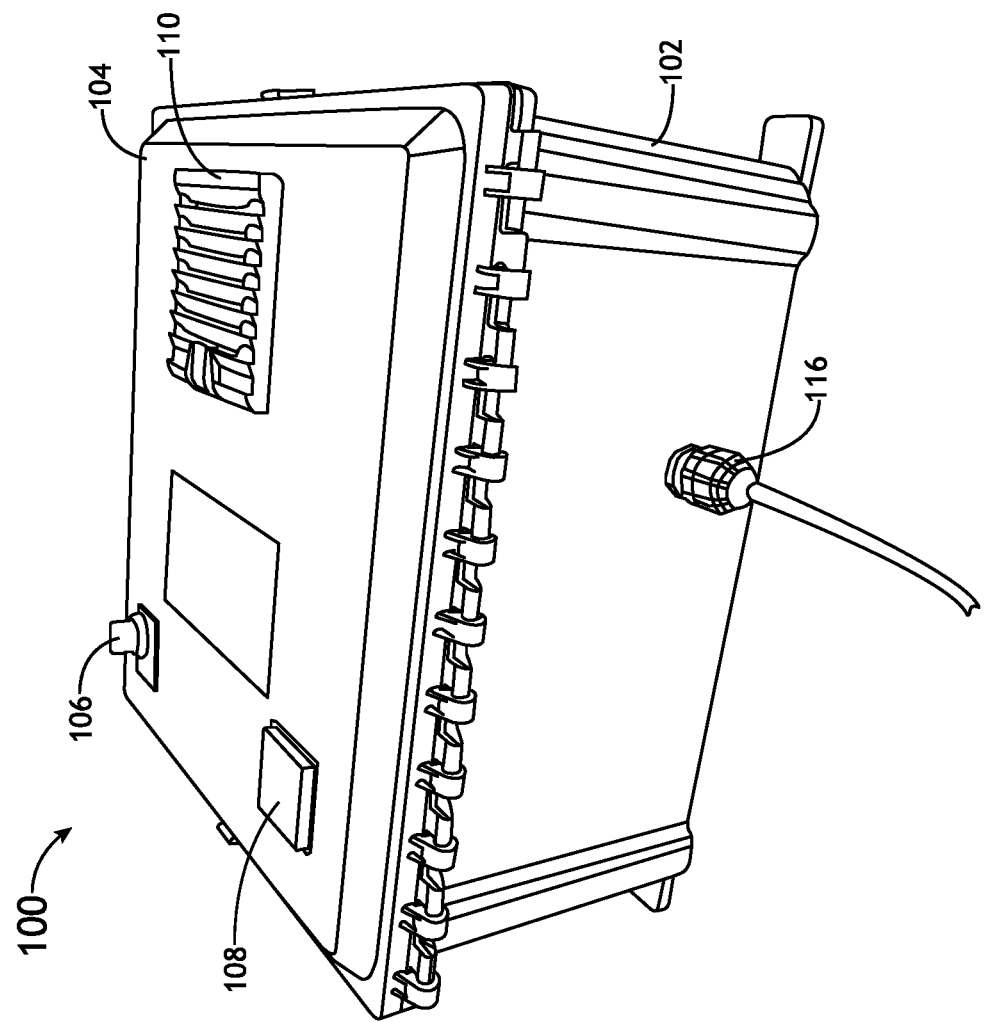
FIG. 3 is a perspective left side view of the air decontaminator of FIG. 1, in accordance with one or more embodiments of this disclosure.
Figure 4:
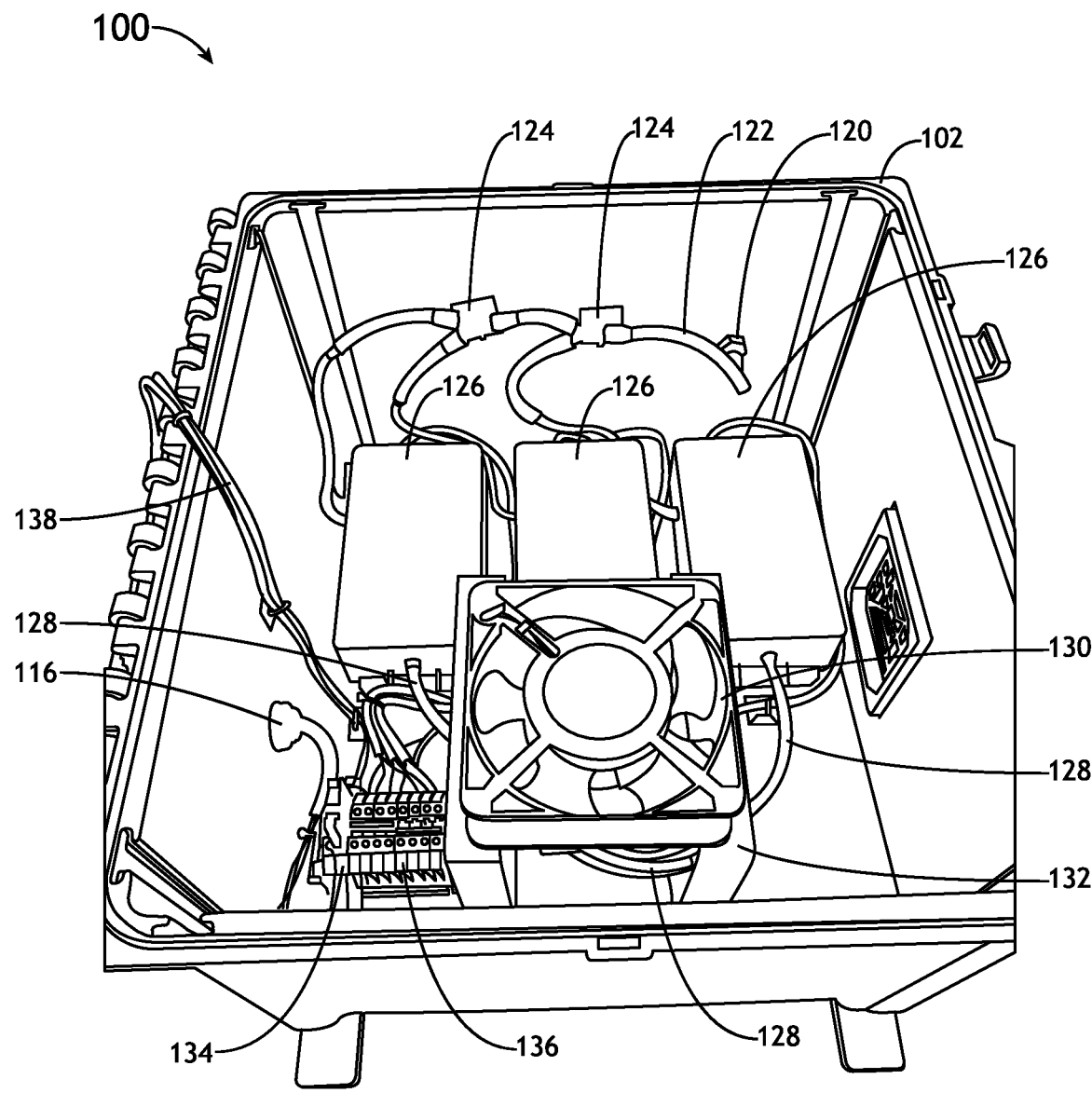
FIG. 4 is a perspective front view of the air decontaminator of FIG. 1 with its lid removed, in accordance with one or more embodiments of this disclosure.

Referring now to FIG. 3, the air decontaminator 100 may include a power cable 116 configured to provide electrical power to one or more components of the air decontaminator 100. For example, the power cable 116 may be configured to provide electrical power from a 120/240V power source (e.g., wall outlet). As shown in FIG. 4, the power cable 116 may connect to internal components of the air decontaminator 100 through a power supply port in the enclosure 102. For example, the power cable 116 may provide electrical power to a power distribution circuit 134 and/or a relay 136. In some embodiments, the power distribution circuit 134 is configured to power the relay 136, which in turn powers and/or controls various components. In other embodiments, the power distribution circuit 134 is alternatively/additionally configured to power one or more components independent of the relay 136. In yet other embodiments, the power distribution circuit 134 and the relay 136 are combined. For example, the relay 136 may include the power distribution circuit 134.

FIG. 4 illustrates the air decontaminator 100 with the lid 104 removed from the enclosure 102. For example, the lid 104 may be partially removed (e.g., swung, slid, or rotated to an open position) or completely removed to expose an interior portion of the enclosure 102. Internal components of the air decontaminator 100 can be seen in FIG. 4 and are described below.

In embodiments, the enclosure 102 includes one or more air intake ports 120 for supplying air to one or more ozone generators 126. The one or more ozone generators 126 are disposed within the enclosure 102 and are fluidically coupled to the one or more air intake ports 120 by tubing 122 (e.g., one or more tubes, pipes, manifolds, or the like). In some embodiments, the tubing 122 includes one or more T or Y connectors 124 (e.g., splitters/combiners) for connecting a plurality of ozone generators 126 to the same air intake port 120. For example, in the embodiment illustrated in FIG. 4, the air decontaminator 100 includes three ozone generators 126 connected to one air intake port 120 using tubing 122 with a plurality of T or Y connectors 124.

Figure 5:
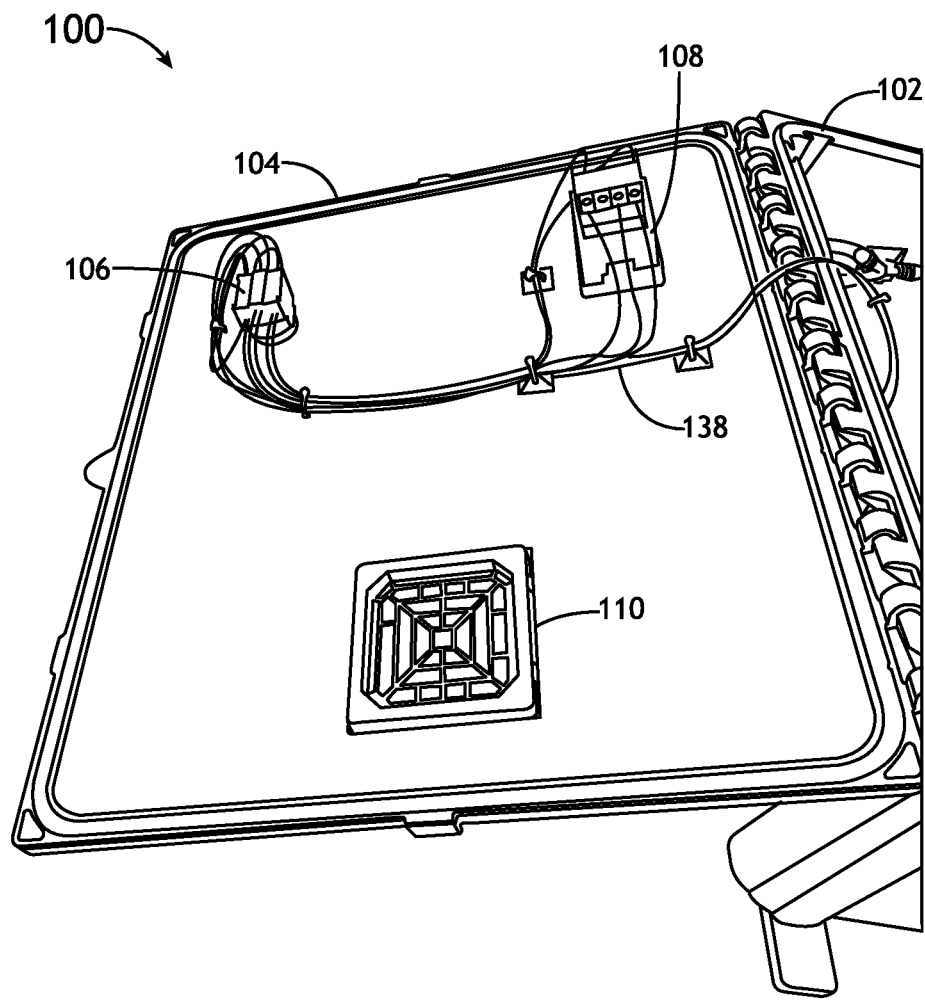
FIG. 5 is a perspective rear view of the lid of the air decontaminator of FIG. 1, in accordance with one or more embodiments of this disclosure.

In embodiments, each of the ozone generators 126 may include a corona discharge tube configured to use oxygen supplied via the air intake port 120 to generate ozone, such as through splitting of oxygen molecules in the air through electrical discharge caused by supplying power to a dielectric material within the corona discharge tube. For example, each ozone generator 126 may include an input port that is fluidically coupled to the air intake port 120 and is configured to convert oxygen from incoming air into ozone. The ozone generators 126 may be powered by the power distribution circuit 134 and/or relay 136. For example, the power distribution circuit 134 and/or relay 136 may provide a power signal to each ozone generator 126 when the electrical switch 106 is in the ON position and/or based on a mechanical or digital timer setting. As shown in FIGS. 4 and 5, the electrical switch 106 and/or user interface device 108 in the lid 104 may be communicatively coupled to the power distribution circuit 134 and/or relay 136 by one or more connectors (e.g., wires, cables, or the like).

In some embodiments, a power signal from the power distribution circuit 134 and/or relay 136 may need to be transformed via a transformer suitable for applying the voltage to the dielectric within the corona discharge tube of the ozone generator 126. For example, a transformer may be coupled to or integrated within the ozone generator 126. In other embodiments, power signals may be directly applied to the ozone generators 126 to power the ozone generators 126. In either case, the ozone generators 126 may be turned off or deactivated by ceasing to provide power signals from the power distribution circuit 134 and/or relay 136.

In some embodiments, the ozone generators 126 may be operated at 110 volts/60 Hz and have an operating frequency of about 450 kHz and 550 kHz, with a power rating of less than about 15 watts, and with a unit performance for electrical consumption of about 32 watts. For example, the ozone generators 126 may have an operating frequency of about 480 kHz. Further, the ozone generators 126 can be provided according to ISO 9001 CE standards.

Each of the ozone generators 126 may be configured to produce from about 800 mg ozone per hour to about 1200 mg ozone per hour, although other ranges may be appropriate depending on the application. In some embodiments, each of the ozone generators 126 produces about 1000 mg ozone per hour. The ozone generators 126 may include other methods and systems for generating ozone, including but not limited to, electrochemical cells configured to generate ozone from water by placing an anode and a cathode in contact with opposite sides of a proton exchange membrane (PEM), and supplying power to the cell, whereby water flowing over the surface of the anode breaks down into hydrogen atoms and oxygen atoms that assemble to form $O_3$ (ozone).

Figure 6:
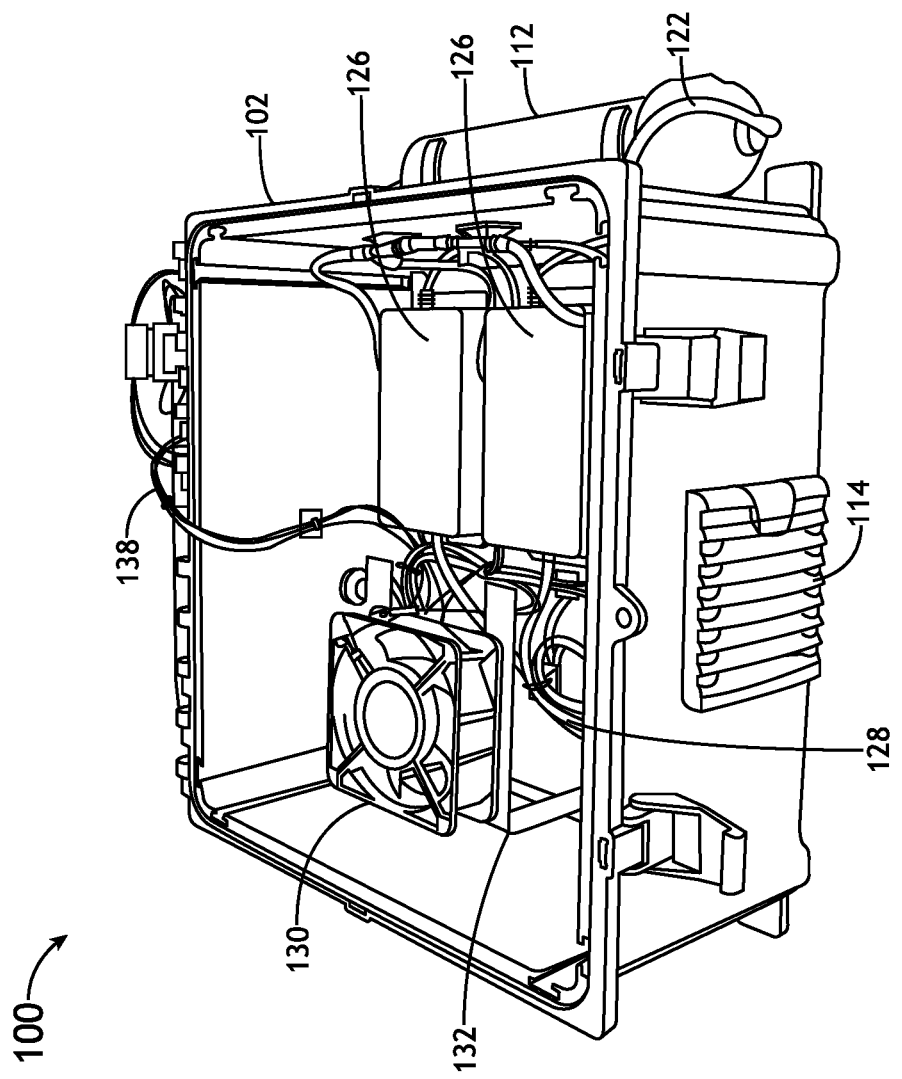
FIG. 6 is a perspective right side view of the air decontaminator of FIG. 1 with its lid removed, in accordance with one or more embodiments of this disclosure.

As shown in FIG. 6, the air decontaminator 100 may further include an air dryer 112 (or filter), which may be externally coupled to the enclosure 102. The air dryer 112 is configured to remove moisture from air before the air is supplied to the ozone generators 126 through the one or more air intake ports 120. The air dryer 112 may be configured to dry the air to a minus dew point by removing water vapor or moisture therefrom, where the water could inhibit the production of ozone by the ozone generators 126.

In some embodiments, the air dryer 112 includes or is coupled to an air compressor. The pressure provided by the compressor can vary depending on the water pressure supplied to the system 100, where the pressure applied by the compressor can be balanced based on the flow rate of air received by the ozone generators 126 via the one or more air intake ports 120. For example, the compressor may be configured to compress the filtered air at least about 15 KPa (e.g., more particularly at a pressure of 18 KPa or about 2.6 psi) to provide a gas throughput in each ozone generator 126 of about 8 SCFH (standard cubic feet per hour). At these pressures, each ozone generator 126 has a residence time of the gas of about three seconds. The pressure applied by the compressor can affect the rate at which the gas flows through an ozone generator 126, which can affect contact time of the air with the components of the ozone generator 126, which can also affect mass gas transfer rates within the ozone generator 126.

The system 100 may further include at least one oxygen concentrator configured to supply oxygen-enriched air to the one or more air intake ports 120 of the air decontaminator 100. In embodiments, an oxygen concentrator may be configured to direct the oxygen-enriched air through the air dryer 112. The oxygen concentrator may also remove moisture from the air. In this regard, the incoming air may undergo two drying stages. The oxygen concentrator may be fluidically coupled to the air decontaminator 100 (e.g., to the air dryer 112 and/or air intake ports 120) by one or more tubes (e.g., flexible tubing, pipes, etc.) for transferring oxygen-enriched air from the oxygen concentrator to the air decontaminator 100.

One or more ozone output tubes 128 are fluidically coupled to the one or more ozone generators 126. The one or more ozone output tubes 128 are configured to release the gaseous ozone (from the ozone generators 126) within the enclosure. For example, each ozone generator 126 may be configured to generate and release ozone via a respective ozone output tube 128. In some embodiments, the air decontaminator 100 includes a plurality of ozone generators 126. For example, in the embodiment illustrated FIG. 4, the air decontaminator 100 includes three ozone generators 126. Each of the ozone generators 126 may have a respective ozone output tube 128, or in some embodiments, two or more of the ozone generators 126 may be fluidically connected in parallel between the air intake port 120 and an ozone output tube 128. For example, splitters/combiners can be used to fluidically couple a pair/set of ozone generators 126 in parallel. The air decontaminator 100 may additionally/alternatively include two or more ozone generators 126 connected in series with one other. Such configurations provide one or more backup ozone generators 126 in case of malfunction or inoperability of one or more of the other ozone generators 126. On average, each ozone generator 126 may have an operating life of about 10,000 working hours.

As previously noted herein, the lid 104 includes a vent 110 through which gaseous ozone may be released from the air decontaminator 100. In some air decontaminators, the lid 104 includes a fan that is coupled to the lid 104 (directly behind the vent 110); however, this arrangement of components often results in noisy operation because the fan movement causes the lid 104 to vibrate against the enclosure 102. To reduce noise by preventing or reducing lid vibrations, the presently disclosed air decontaminator 100 does not have a fan coupled to the lid 104. Instead, as shown in FIGS. 4 through 8, the air decontaminator 100 includes a fan 130 that is suspended below the vent 110 by a support frame 132 that is coupled to an inner surface of the enclosure 102.

The fan 130 is disposed within the enclosure 102 and is configured to blow gaseous ozone out from the enclosure 102 through the vent 110 in the lid 104. For example, the one or more ozone output tubes 128 may be configured to release ozone below/behind the fan 130 so that the ozone is blown by the fan 130 through the vent 110 when the fan 130 is active. The support frame 132 is configured to suspend the fan 130 over the one or more ozone output tubes 128 and at a distance from the lid 104 in order to prevent or reduce lid vibrations caused by fan movement when the fan 130 blows the ozone through the vent 110 in the lid 104.

In embodiments, the flow may be as follows: the one or more ozone generators 126 output gaseous ozone through the one or more ozone output tubes 128; the ozone output tubes 128 release the ozone below/behind the fan 130; and the fan 130 blows the ozone through the vent 110 so that the ozone is blown into ambient air surrounding the air decontaminator 100.

Figure 7:
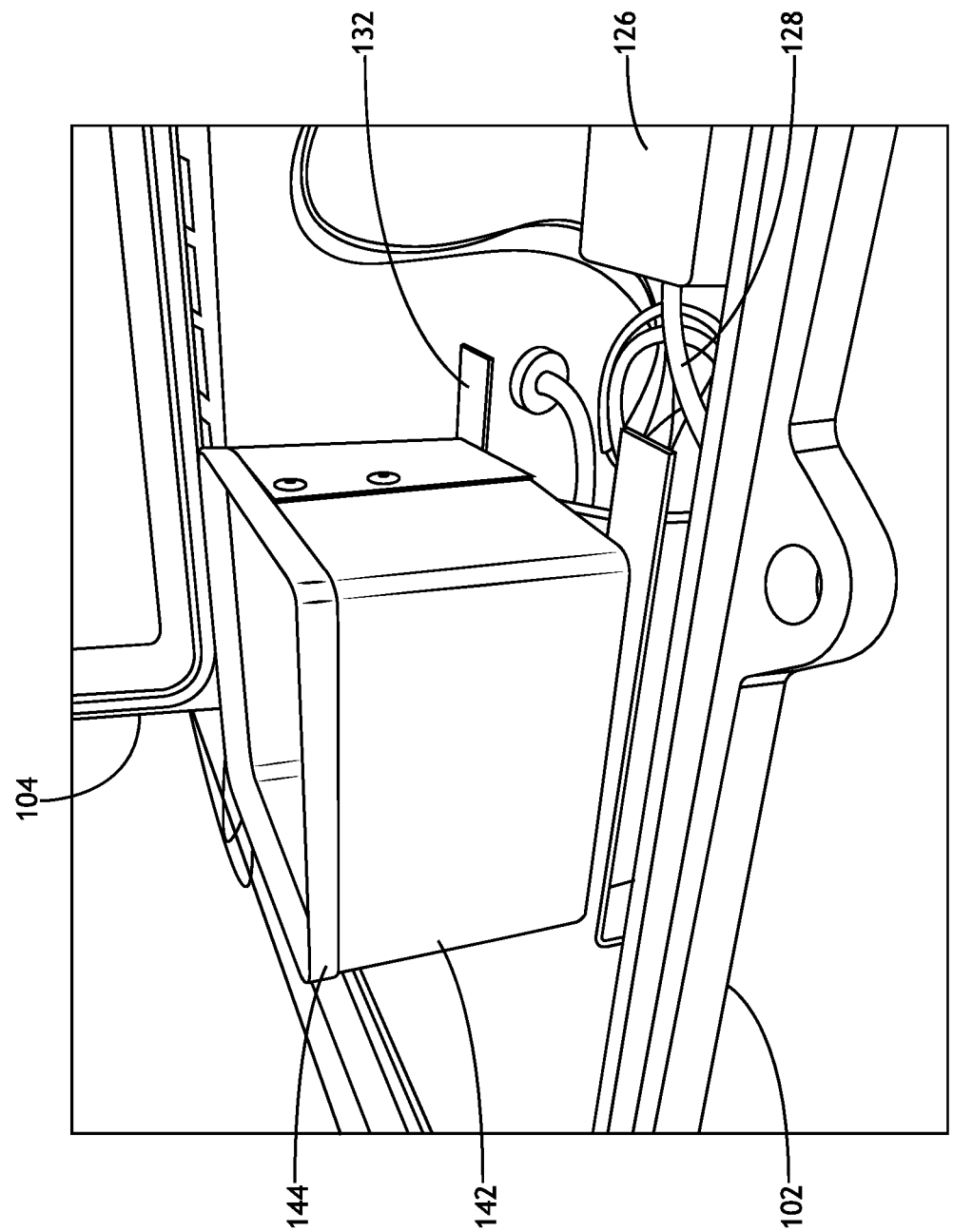
FIG. 7 is a zoomed-in partial view of the air decontaminator of FIG. 1, wherein the air decontaminator includes a duct configured to extend from an inner fan to a vent in the lid (when the lid is closed), in accordance with one or more embodiments of this disclosure.

As shown in FIG. 7, in some embodiments, the air decontaminator 100 further includes a duct 142 configured to extend from the fan 130 to the vent 110 in the lid 104 when the lid 104 is closed and/or secured to the enclosure 102. The duct 142 helps direct the ozone from the fan 130 through the vent 110. For example, the flow may be as follows: the one or more ozone generators 126 output gaseous ozone through the one or more ozone output tubes 128; the ozone output tubes 128 release the ozone below/behind the fan 130; the fan 130 blows the ozone through the duct 142; and the duct 142 directs the ozone through the vent 110 so that the ozone is blown into ambient air surrounding the air decontaminator 100.

In some embodiments, the duct 142 includes a gasket 144 (e.g., a rubber/foam rim) disposed at an end of the duct 142 to help seal a junction between the duct 142 and the vent 110 in the lid 104. The gasket 144 may help prevent ozone leakage at the duct-vent junction and can also dampen any vibrations caused by contact between the duct 142 and the lid 104.

The duct 142 may be configured to surround the fan 130. For example, the duct 142 may at least partially encircle the fan 130 like a sleeve. In some embodiments, the duct 142 further includes a gasket between the fan 130 and the duct 142 (e.g., a rubber/foam rim around the fan 130) to prevent ozone leakage at the duct-fan interface and/or to dampen any vibrations caused by contact between the duct 142 and the fan 130.

Figure 8:
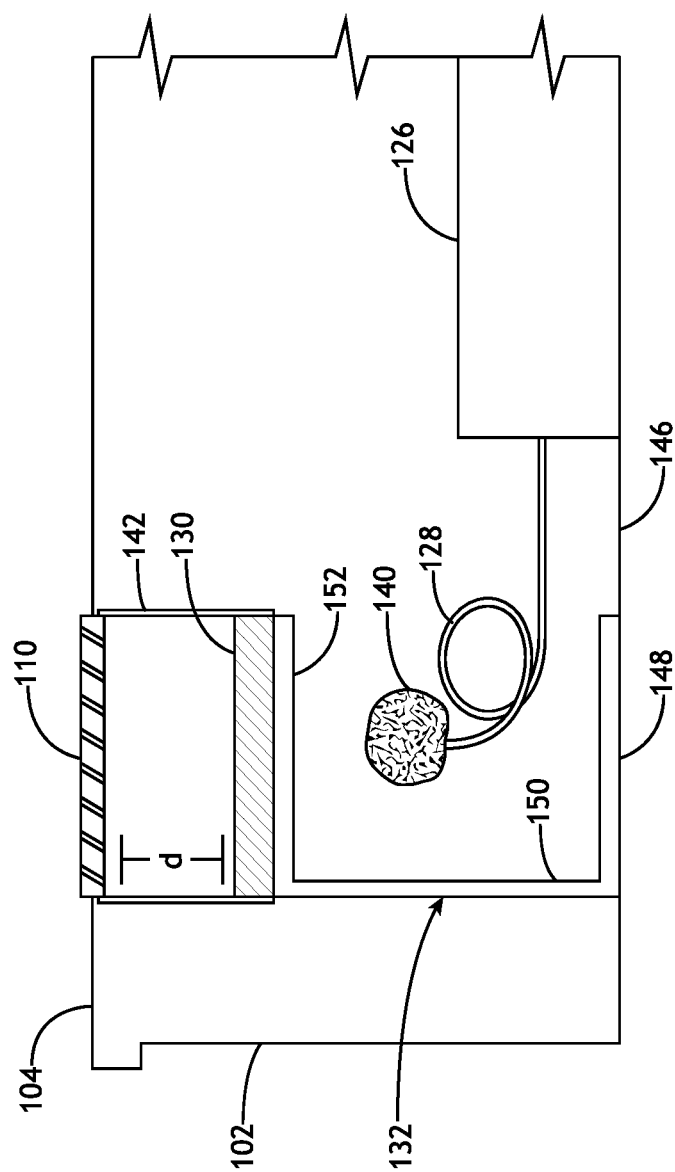
FIG. 8 is a partial cross-sectional view of the air decontaminator of FIG. 1, in accordance with one or more embodiments of this disclosure.

Referring now to FIG. 8, the support frame 132 is configured to suspend the fan 130 over the one or more ozone output tubes 128. For example, the one or more ozone output tubes 128 may be at least partially tucked underneath/behind the fan 130 so that the ozone is released within an air flow path of the fan 130. In some embodiments, each ozone output tube 128 includes a diffuser 140 disposed at a distal (release) end of the ozone output tube 128 so that gaseous ozone can be diffused (e.g., spread) out from the distal end of the ozone output tube 128 into the air flow path of the fan 130. Although FIG. 8 only depicts one ozone generator 126, ozone output tube 128, and diffuser 140, it is to be understood that the air decontaminator 100 can include any number of (e.g., 2, 3, or more) ozone generators 126, ozone output tubes 128, and diffusers 140 that are similarly arranged.

In embodiments, the support frame 132 includes: a first portion 148 coupled to an inner surface 146 of the enclosure 102; a second portion 150 perpendicular to the first portion 148 (e.g., extending up/out from the inner surface 146 of the enclosure 102), and a third portion 152 perpendicular to the second portion 150 (e.g., extending across a portion of the inner surface 146 of the enclosure 102 at an elevation/distance from the inner surface 146 of the enclosure 102). In this regard, the first portion 148, second portion 150, and third portion 152 of the support frame 132 form a U-shaped structure.

The fan 130 is mounted to the third portion 152 of the support frame 132 such that the fan 130 is suspended below/behind the vent 110 in the lid 104 and at an elevation/distance from the inner surface 146 of the enclosure 102. The support frame 132 is configured to suspend the fan 130 at a distance (d) from the lid 104 in order to prevent or reduce lid vibrations caused by fan movement when the fan 130 blows the ozone through the vent 110 in the lid 104. In some embodiments, the distance (d) between the fan 130 and the lid 104 is at least one inch (e.g., 1 to 3 inches, or more). In other embodiments, a shorter distance (d) between the fan 130 and the lid 104 may be appropriate depending on application requirements. For example, a shorter distance (d) may appropriate if the air decontaminator 100 is configured to run at a lower power or if other noise dampening mechanisms are used in conjunction with the fan configuration described herein.

In embodiments, the electrical switch 106, user interface device 108, ozone generators 126, and fan 130 are all coupled to the relay 136. The relay 136 may be configured to distribute incoming signals (e.g., power, communication, and/or control signals) to the ozone generators 126 and fan 130 based on control signals from the electrical switch 106 and/or user interface device 108. In this regard, the relay 136 may include one or more switches or switchboards configured to transmit and receive signals via connectors (e.g., wires, cables, optical fibers, etc.). In some embodiments, the relay 136 may further include a controller (e.g., microcontroller, microprocessor, or any other programmable logic device (PLD)) or hardwired logic device.

The relay 136 may be configured to send and/or receive control signals based on the electrical switch 106 and/or user interface device 108. In some embodiments, the control signals may comprise power signals for the one or more ozone generators 126 and the fan 130. For example, the electrical switch 106 may cause the relay 136 to provide power for the one or more ozone generators 126 and fan 130 when the electrical switch 106 is in the ON/TIMER position. In some embodiments, the control signals are based on a user input (e.g., runtime) that causes the relay 136 to run or stop running the one or more ozone generators 126 and fan 130 based on a mechanical/digital timer circuit.

In some embodiments, the electrical switch 106 and/or user interface device 108 may be configured to close/complete a circuit that allows power signals to flow to the one or more ozone generators 126 and fan 130 when the electrical switch 106 is in the ON position and/or in an active TIMER position. Alternatively, the electrical switch 106 and/or user interface device 108 may be configured to provide a control signal (e.g., binary/discrete signal (e.g., a "1" or "0"), HIGH/LOW voltage signal, or the like) that causes a switch and/or controller in the relay 136 to close/complete a circuit that allows power signals to flow through the relay 136 to the one or more ozone generators 126 and fan 130 when the electrical switch 106 is in the ON position and/or in an active TIMER position.

Although the invention has been described with reference to embodiments illustrated in the attached drawings, equivalents or substitutions may be employed without departing from the scope of the invention as recited in the claims. Components illustrated and described herein are examples of devices and components that may be used to implement embodiments of the present invention and may be replaced with other devices and components without departing from the scope of the invention. Furthermore, any dimensions, degrees, and/or numerical ranges provided herein are to be understood as non-limiting examples unless otherwise specified in the claims.

What is claimed is:

1. An air decontaminator, comprising:
   an enclosure;
   a lid removably coupled to the enclosure, the lid including a vent;
   one or more ozone generators disposed within the enclosure, the one or more ozone generators configured output gaseous ozone;
   one or more ozone output tubes fluidically coupled to the one or more ozone generators, the one or more ozone output tubes configured to release the gaseous ozone within the enclosure;
   a fan configured to blow the gaseous ozone through the vent in the lid; and
   a support frame configured to suspend the fan over the one or more ozone output tubes and at a distance from the lid in order to reduce lid vibrations cause by fan movement when the fan blows the gaseous ozone through the vent in the lid.

2. The air decontaminator of claim 1, further comprising a duct extending from the fan to the vent in the lid.

3. The air decontaminator of claim 2, further comprising a gasket disposed at an end of the duct to seal a junction between the duct and the vent in the lid.

4. The air decontaminator of claim 1, wherein the support frame comprises a first portion coupled to an inner surface of the enclosure, a second portion perpendicular to the first portion, and a third portion perpendicular to the second portion, wherein the fan is mounted to the third portion of the support frame.

5. The air decontaminator of claim 4, wherein the first, second, and third portions of the support frame form a U-shaped structure.

6. The air decontaminator of claim 1, wherein the fan is suspended at least one inch from the lid.

7. The air decontaminator of claim 6, wherein the fan is suspended one to three inches from the lid.

8. The air decontaminator of claim 1, further comprising:
   an electrical switch; and
   a relay configured to power the one or more ozone generators and the fan when the electrical switch is toggled.

9. The air decontaminator of claim 8, wherein the electrical switch is a timer switch.

10. The air decontaminator of claim 8, further comprising:
    a user interface device configured to receive a runtime input for the timer switch.

11. An air decontaminator, comprising:
    an enclosure;
    a lid hingedly coupled to the enclosure, the lid including a vent;
    one or more ozone generators disposed within the enclosure, the one or more ozone generators configured output gaseous ozone;
    one or more ozone output tubes fluidically coupled to the one or more ozone generators;
    one or more diffusers coupled to the one or more ozone output tubes, the one or more diffusers configured to release the gaseous ozone within the enclosure;
    a fan configured to blow the gaseous ozone through the vent in the lid; and
    a support frame configured to suspend the fan over the one or more diffusers and at a distance from the lid in order to reduce lid vibrations cause by fan movement when the fan blows the gaseous ozone through the vent in the lid.

12. The air decontaminator of claim 11, further comprising a duct extending from the fan to the vent in the lid.

13. The air decontaminator of claim 12, further comprising a gasket disposed at an end of the duct to seal a junction between the duct and the vent in the lid.

14. The air decontaminator of claim 11, wherein the support frame comprises a first portion coupled to an inner surface of the enclosure, a second portion perpendicular to the first portion, and a third portion perpendicular to the second portion, wherein the fan is mounted to the third portion of the support frame.

15. The air decontaminator of claim 14, wherein the first, second, and third portions of the support frame form a U-shaped structure.

16. The air decontaminator of claim 11, wherein the fan is suspended one to three inches from the lid.

17. The air decontaminator of claim 11, further comprising:
   an electrical switch; and
   a relay configured to power the one or more ozone generators and the fan when the electrical switch is toggled.

18. The air decontaminator of claim 17, wherein the electrical switch is a timer switch.

19. The air decontaminator of claim 17, further comprising:
   a user interface device configured to receive a runtime input for the timer switch.

20. An air decontaminator, comprising:
   an enclosure;
   a lid removably coupled to the enclosure, the lid including a vent;
   a plurality of generators disposed within the enclosure, the plurality of ozone generators configured output gaseous ozone;
   a plurality of ozone output tubes fluidically coupled to the plurality of ozone generators, the plurality of ozone output tubes configured to release the gaseous ozone within the enclosure;
   a fan configured to blow the gaseous ozone through the vent in the lid; and
   a support frame configured to suspend the fan over the plurality of ozone output tubes and at a distance from the lid in order to reduce lid vibrations cause by fan movement when the fan blows the gaseous ozone through the vent in the lid.

* * * * *